United States Patent
Wagner (10) Patent No.: US 10,161,936 B2
(45) Date of Patent: Dec. 25, 2018

(54) METHOD AND KIT FOR CYTOKINE ANALYSIS FROM A HUMAN WHOLE BLOOD SAMPLE

(71) Applicant: UNIVERSITY OF LEIPZIG, Leipzig (DE)

(72) Inventor: Ulf Wagner, Leipzig (DE)

(73) Assignee: UNIVERSITY OF LEIPZIG, Leipzig (DE)

( * ) Notice: Subject to any disclaimer, the term of this patent is extended or adjusted under 35 U.S.C. 154(b) by 0 days.

(21) Appl. No.: 14/773,202

(22) PCT Filed: Mar. 7, 2014

(86) PCT No.: PCT/EP2014/054406
§ 371 (c)(1),
(2) Date: Sep. 4, 2015

(87) PCT Pub. No.: WO2014/135668
PCT Pub. Date: Sep. 12, 2014

(65) Prior Publication Data
US 2016/0011192 A1 Jan. 14, 2016

(30) Foreign Application Priority Data
Mar. 8, 2013 (DE) .......... 10 2013 204 046

(51) Int. Cl.
*G01N 33/564* (2006.01)

(52) U.S. Cl.
CPC ..... *G01N 33/564* (2013.01); *G01N 2333/525* (2013.01); *G01N 2333/545* (2013.01); *G01N 2333/5412* (2013.01); *G01N 2333/5421* (2013.01); *G01N 2333/5428* (2013.01); *G01N 2333/57* (2013.01); *G01N 2800/102* (2013.01); *G01N 2800/52* (2013.01)

(58) Field of Classification Search
None
See application file for complete search history.

(56) References Cited

PUBLICATIONS

Zivojinovic et al, Inflammopharmacology, 2012, vol. 20, pp. 323-330.*
Rossol et al, (The Journal of Immunology, 2007, vol. 179, pp. 4239-4248.*
Thurm et al, Current Protocols in Immunology; 2005, pp. 1-12.*
International Search Report, issued in PCT/EP2014/054406, dated Apr. 16, 2014.
Alex et al., "Multiplex serum cytokine monitoring as a prognostic tool in rheumatoid arthritis," Clinical and Experimental Rheumatology 25(4):584-592 (2007).
Holmgren et al., "Evaluation of the use of anti-TNF-alpha n an LPS-induced murine movel," Journal of Reproductive Immunology, 78(2):134-139 (2008) (abstract only).
Holmgren et al., "Evaluation of the use of anti-TNF-a in an LPS-induced murine model," Journal of Reproductive Immunology, 78:134-139 (2008).

* cited by examiner

*Primary Examiner* — Joanne Hama
*Assistant Examiner* — Fozia Hamud
(74) *Attorney, Agent, or Firm* — Heslin Rothenberg Farley and Mesiti, PC (57) ABSTRACT

The invention relates to a method for prognostic evaluation of the disease progression of rheumatoid arthritis, in particular prognostic evaluation of the disease progression during treatment, and for the diagnosis and/or activity determination of rheumatoid arthritis by analysing cytokines from a human full blood sample. In the method according to the invention, a volume of a full blood sample of a human is transferred into at least one test tube containing a stimulating agent. As control samples, the same volume of a full blood sample of the human in each case is transferred into an empty test tube as a negative control and a test tube containing lipopolysaccharide as a positive control respectively. After incubation, the concentration of at least one proinflammatory cytokine is determined from the cell-free residue of each test tube. By way of an altered concentration of the at least one cytokine in the at least one test tube comprising the stimulating agent, the prognostic evaluation of the disease progression or the diagnosis is subsequently made.

The invention further relates to an associated diagnostic kit and to the use thereof. The invention is applied in medical diagnostics and medical research.

8 Claims, 6 Drawing Sheets

METHOD AND KIT FOR CYTOKINE ANALYSIS FROM A HUMAN WHOLE BLOOD SAMPLE

CROSS REFERANCE TO RELATED APPLICATIONS

This application is a U.S. National Phase filing under 35 U.S.C. § 371 of International Application No PCT/EP 2014/054406, filed Mar. 7, 2014, and published as WO 2014/135668-A1 on Sept. 12, 2014, which claims benefit of priority from German Patent Application Ser. No. DE 10 2013 204 046.6, filed Mar. 8, 2013. The entire contents of each of the prior applications are incorporated herein by reference in their entirety.

FIELD OF APPLICATION

The invention relates to a method for prognostic evaluation of the disease progression of rheumatoid arthritis, in particular prognostic evaluation of the disease progression during treatment, and for the diagnosis or activity determination of rheumatoid arthritis by analysing cytokines from a human full blood sample. The invention further relates to an associated diagnostic kit and to the use thereof. The invention is applied in medical diagnostics and medical research.

BACKGROUND OF THE DISCLOSURE

Rheumatoid arthritis (RA) is a chronic autoimmune disease of the joints. As well as afflicting the joints, the disease may also affect internal organs and the cardiovascular system. Thus far, the causes of the disease are largely unexplained. For diagnosis, the presence of autoantibodies in a patient's serum is presently used, among other things. In addition to detecting the rheumatoid factor (autoantibodies against endogenous IgG molecules), detecting anti-CCP antibodies, which act against citrullinated side chains of proteins, makes earlier diagnosis of RA possible (Schellekens 1998). A comparably high sensitivity can be achieved by detecting mutated citrullinated vimentin, MCV (Poulsom 2008). Commercial test kits are already available for detecting both anti-CCP antibodies and anti-MCV antibodies, and make possible simple, rapid detection of the antibodies and thus a prediction as to the diagnosis of RA. However, evaluation of the stage of the disease, in particular the state of the joint destruction, is only possible to a very limited extent by detecting the autoantibodies systemically present in the blood.

It is therefore desirable to use RA diagnostics which take into account the activation status of the immune cells involved in the disease. It is known that particular cell populations of the immune cells, such as T cells or monocytes, secrete different cytokines depending on the disease stage of the RA, said cytokines making it possible to make a prediction as to the progress of the RA. It is also known that these cells also circulate in the patient's circulatory system in a small amount.

It has been observed that different cytokine levels can be found in RA patients from in healthy controls as a result of stimulation of suitable signal transduction paths of cells of the immune system. Meusch 2009 states that the signal emission via transmembrane TNF-α (tumour necrosis factor, for which the common abbreviation "TNF-α" is used herein) in monocytes from the RA patient's blood is associated with increased IL-1β formation. For this purpose, monocytes are initially isolated from the patient's blood, counted, and subsequently cultivated at a defined number in cell culture medium in the presence of anti-TNF-α, the IL-1β level subsequently being determined by ELISA.

It is further desirable to be able to make a prognostic prediction as to the disease progression by simple test methods. Prognosis as to a patient's response to a particular form of treatment is particularly desirable.

For clinical use, it is worthwhile to provide easy-to-use test systems and corresponding methods which make it possible to carry out the respectively desired detection in as few method steps as possible, at a low equipment cost but still to a high precision.

SUMMARY OF THE DISCLOSURE

The object of the invention is therefore to provide a method and a test system, for analysing the production of proinflammatory cytokines of immune cells from samples of potential patients having rheumatoid arthritis, which make possible prognostic prediction as to the disease progression, in particular prognostic evaluation of the disease progression during treatment, or diagnosis. The method should be simple and reproducible and make possible the earliest possible diagnosis or prognostic evaluation.

The object is achieved according to the invention by a method for prognostic evaluation of the disease progression of rheumatoid arthritis, in particular the prognostic evaluation of the disease progression during treatment (in particular during treatment using a TNF-inhibiting drug), in which cytokine analysis takes place from a human full blood sample. In the method according to the invention, the following method steps are carried out:

A volume of a full blood sample of a human is transferred into at least one test tube containing a stimulating agent. Preferably, the full blood sample is transferred into the test tube immediately after being taken. The volume of full blood sample used is preferably 3-8 ml, preferably 3-5 ml. As control samples, the same volume in each case of a full blood sample of the human is transferred into an empty test tube as a negative control and a test tube containing lipopolysaccharide as a positive control respectively.

The respective test tubes along with the full blood samples contained therein (positive control, negative control and the at least one test tube containing the stimulating agent) are subsequently incubated at a temperature of 30-40° C., preferably 36-38° C., preferably for several hours, preferably 4-48 h, more preferably 12-24 h.

Subsequently, the cell-free residue of each full blood sample is obtained from the respective test tubes. From the cell-free residue, the concentration of at least one proinflammatory cytokine is determined. In this context, the concentration of at least one of the following cytokines is determined: TNF-α, IL-8, IFNγ, IL-10, IL-1β and IL-6. It is also possible to determine the concentration of one or more dissolved receptors, preferably selected from TNFR1, TNFR2, IL1R antagonist, IL-1R1, IL-1R2.

By way of an altered concentration of the at least one cytokine in the at least one test tube comprising the stimulating agent, the prognostic evaluation of the disease progression of rheumatoid arthritis is subsequently carried out by comparison with the negative control, in particular the prognostic evaluation of the disease progression of rheumatoid arthritis during treatment using a TNF-blocking drug (what is referred to as the "treatment response").

As an alternative or in addition to the prognostic evaluation of the disease progression of rheumatoid arthritis, in particular the prognostic evaluation of the treatment response of rheumatoid arthritis to TNF-blocking drugs (tumour-necrosis-factor-blocking drugs, previously "tumour-necrosis-factor-alpha"-blocking drugs), the invention is used to make the diagnosis of rheumatoid arthritis using the altered concentration of the cytokines in the test tube containing the stimulating agent. Alternatively or in addition, the invention is used to make a prognostic prediction as to the severity of joint destruction in relation to rheumatoid arthritis.

DETAILED DESCRIPTION OF THE DISCLOSURE

The invention provides a method by means of which it is possible to make a prognosis of the disease progression of rheumatoid arthritis and/or the diagnosis of rheumatoid arthritis using the concentration of the cytokines secreted by cells of a human's peripheral blood. It is particularly surprising that it is possible to carry out the analysis using a human full blood sample and that no further isolation of discrete cell populations (for example monocytes or T cells) from the full blood sample is necessary. Since the cells which secrete the cytokines to be detected, in particular monocytes and T cells, are contained in full blood at low concentrations, it was extremely surprisingly that detectable cytokine levels were obtained when a method according to the invention was carried out on the cell-free residue (in other words the cytokine-enriched plasma). It is thus possible to obtain the cell-free residue from each individual test tube after the full blood samples are incubated, without the respectively tested full blood sample having to be transferred between a plurality of vessels during the method (what is referred to as an "in-tube" method). The method can thus be carried out in an extremely simple manner at a low equipment cost.

It is further surprising that prognostic evaluation of the disease progression, in particular prognosis of a treatment response for rheumatoid arthritis, can be carried out using an altered cytokine production of cells in the peripheral blood. The method according to the invention is thus suitable in particular for prognosis of the patient's response to a treatment using a TNF-inhibiting drug (FIGS. 1 to 7). Surprisingly, the inventors were able to demonstrate that an altered cytokine production in the event of specific stimulation of discrete signal transduction paths exhibits an association with the disease progression after treatment using a TNF inhibitor.

According to the invention, the method according to the invention uses a full blood sample, that is to say a human blood sample. Said full blood sample is preferably mixed with the anticoagulant heparin. Further purification and isolation of discrete cell populations is not necessary. The full blood sample therefore comprises all of the cells and plasma naturally present in blood. In particular, the following cells are contained in the full blood sample: erythrocytes, thrombocytes and leukocytes, specifically neutrophilic, eosinophilic and basophilic granulocytes, lymphocytes and monocytes. The full blood sample is preferably used immediately after being taken, preferably at most 60 minutes, preferably at most 30 minutes after being taken from the potential patient.

The test tubes used for the invention are test tubes suitable for cell culture, preferably test tubes made of an inert plastics material, preferably polystyrene, which have a hydrophilic surface. The volume of a test tube is preferably 5-15 ml, preferably 5-10 ml. On the surface of the inert plastics material, on the inside of the test tube, there is preferably a coating of a bioactive protein, preferably collagen, fibrinogen or fibronectin, so as to produce favourable cell culture conditions. What is referred to as an "empty test tube" is used as a negative control. Within the meaning of the invention, the empty test tube is understood to be a test tube suitable for cell culture, which is preferably of the above-stated dimensions and preferably has an above-described coating, and which does not contain any further agents, in particular any agents which stimulate the cytokine production of cells of the immune system. A test tube which contains bacterial lipopolysaccharides (LPSs) is used as a positive control. These are present either as a constituent of a coating on the inner face of the test tube or as a solid or an aqueous solution within the test tube. Thus, the test tube preferably contains enough LPS that after the defined volume of the full blood sample is transferred, a concentration of 80-120 ng/ml LPS is achieved in the liquid. Preferably, the test tube for the positive control contains 200-900 ng LPS.

More preferably, the test tubes, meaning those for the positive control and negative control and also the at least one test tube comprising a stimulating agent, are designed as blood sampling tubes. This makes it possible to withdraw the full blood sample directly into the test tube. In this context, it is particularly preferred for the blood sampling tube to be designed in accordance with the negative pressure system. In this case, there is a negative pressure in the test tube from the outset, which causes the blood to be sucked up. Using the negative pressure system, more reproducible volumes can be transferred into the test tube when the blood is taken than if the blood is taken in accordance with the aspiration system (in which a negative pressure is generated by pulling a plunger out when taking the blood). Alternatively, using the test tubes, full blood samples of defined volumes could be transferred out of previously taken full blood (for example from a blood bag).

In one of the test tubes there is what is referred to as a "stimulating agent". Within the meaning of the invention, a stimulating agent is understood to be a substance which is suitable for activating a discrete signal transduction path in a cell of the immune system, the secretion of cytokines by the respective cell being influenced when the signal transduction path is activated. By contrast, the stimulating agent does not involve substances which non-specifically excite a plurality of signal transduction paths. In particular, the stimulating agent is not a TLR ligand, in particular not an LPS. Preferably, the stimulating agent is selected from anti-TNF-α, a TNF-R2:Ig fusion protein, a ligand of CCR5 (preferably RANTES (also known as "CCL5") or MIP-1α (also known as "CCL3")) and a divalent or trivalent cation, preferably in the form of a soluble salt of calcium, aluminium, gadolinium, strontium or magnesium.

In a preferred embodiment of the invention, in parallel with the specific activation of a signal transduction path by the stimulating agent, "non-specific priming" of the cells takes place via toll-like receptors (TLRs). For this purpose, the test tube comprising the stimulating agent additionally contains at least one toll-like receptor ligand, preferably selected from LPS, dead bacteria, ssRNA, dsRNA, CpG-oligonucleotides, zymosan and heat shock proteins. Preferably, the test tube comprising the stimulating agent contains a non-activating concentration of a TLR ligand for the non-specific priming with the TLR ligand. Within the meaning of the invention, a non-activating concentration of a TLR ligand is understood to mean an amount of the TLR ligand which is not sufficient per se to make possible non-specific excitation of signal transduction paths in the cells. More preferably, the test tube comprising the stimulating agent therefore contains a TLR ligand in an amount such that when the test tube is filled with the full blood sample, a concentration of at most 1 ng/ml (concentration based on the amount of TLR ligand per millilitre of full blood sample) is achieved, particularly preferably at most 0.1 ng/ml, more preferably 0.01 to 1 ng/ml, most preferably 0.01 to 0.1 ng/ml. Preferred TLR ligands which are used for the non-specific priming are selected from LPS, heat-killed *Listeria monocytogenes*, ssRNA40, tenascin or flagellin. LPS is particularly preferred. Using the non-activating concentration, the non-specific priming advantageously improves the reaction of the cells to the specific stimulation. Surprisingly, by comparison with exclusively specific stimulation of the cells using the stimulating agent (without non-specific priming), this embodiment of the invention achieves particularly reproducible results by way of the addition of the low-concentration TLR ligand.

After cultivation, the cell-free residue of the cultivated full blood samples is obtained, preferably by centrifugation. From the residue, the concentration of at least one, preferably at least two, preferably at least three, of the cytokines TNF-$\alpha$, IL-8, IFN$\gamma$, IL-10, IL-1$\beta$ and/or IL-6 is determined. It is also possible to determine the concentration of one or more dissolved receptors, preferably selected from TNFR1, TNFR2, IL1R antagonist, IL-1R1, IL-1R2. The concentration of cytokines or dissolved receptors can be determined by various known methods, such as ELISA or cytometric bead assays. Because of the ease of use, an ELISA is preferably used to determine the cytokine concentration.

In the invention, the specific activation of a particular signal transduction path in monocytes of a patient, which are present in a full blood sample, is used to create a cytokine profile, by means of which the prognostic evaluation of the disease progression and/or the diagnosis of rheumatoid arthritis is carried out. The following three analyses are particularly suitable, and thus preferred, for the invention, and each individually make possible prognostic evaluation of the disease progression and/or diagnosis of rheumatoid arthritis. Preferably, at least two of the following analyses are carried out in the invention.

First analysis: comparison of the spontaneous secretion of proinflammatory cytokines with the secretion of proinflammatory cytokines after cross-linking the transmembrane TNF-$\alpha$ with a specific binding partner of transmembrane TNF-$\alpha$ (tmTNF-$\alpha$). Said specific binding partner is preferably anti-TNF-$\alpha$ or a TNF-R2:Ig fusion protein.

For said first analysis, a specific binding partner of tmTNF-$\alpha$ is contained in a test tube as a stimulating agent. Preferably, the test tube contains 50-300 µg/ml, more preferably 75-125 µg/ml, of the specific binding partner of tmTNF-$\alpha$. Said test tube preferably additionally contains a non-activating amount of a TLR ligand, in particular as described above.

The specific binding partner of tmTNF-$\alpha$ may be either surface-bonded or dissolved. Preferably, the specific binding partner of tmTNF-$\alpha$ is used in a surface-bonded form. If the specific binding partner is bonded, a soluble form of the specific binding partner is preferably additionally added, for a final concentration in the culture medium of 30-50 µg/ml, preferably 40 µg/ml. If the specific binding partner is exclusively in dissolved form, the final concentration thereof in the culture medium is preferably 40 µg/ml.

From the cell-free residue of the full blood samples from the test tubes, in said first analysis, the concentration of at least two, preferably at least three, of the cytokines TNF-$\alpha$, IL-8, IFN$\gamma$, IL-10 and IL-1$\beta$, more preferably all of said cytokines, is determined. Optionally, the concentration of at least one of the cytokines IL-6, IFN-$\alpha$, IFN-1$\alpha$, IL-12, IL-23 and IL-4 is additionally determined. It is also possible to determine the concentration of one or more dissolved receptors, preferably selected from TNFR1, TNFR2, IL1R antagonist, IL-1R1, IL-1R2.

Said first analysis is based on the observation that monocytes of patients having rheumatoid arthritis already spontaneously secrete proinflammatory cytokines, in particular IL-1$\beta$, TNF-$\alpha$, TNFR1 and IL-8. Cross-linking the transmembrane TNF-$\alpha$ with the specific binding partner of tm-TNF-$\alpha$ has an inhibitory effect on the secretion of IL-1$\beta$. Therefore, in said first analysis, an increased spontaneous IL-1$\beta$ production in the negative control and a lower concentration of IL-1$\beta$ in the residue of the sample from the test tube comprising the specific binding partner of tm-TNF-$\alpha$ by comparison with the negative control both indicate a risk that rheumatoid arthritis is present.

For the following cytokines, an increased concentration in the residue of the sample from the test tube comprising the specific binding partner of the transmembrane TNF-$\alpha$ by comparison with the negative control indicates an increased risk of the presence of RA: TNF-$\alpha$, IL-8, IFN$\gamma$, IL-6, INF$\alpha$, IL-1$\alpha$, IL-23.

A cytokine concentration of preferably 200 pg/ml, more preferably 500 pg/ml, of the cytokines TNF-$\alpha$ and IL-8 in the residue of the sample from the test tube comprising the specific binding partner of the transmembrane TNF-$\alpha$ indicates a pathological finding.

For the following cytokines, a reduced concentration in the residue of the sample from the test tube comprising the specific binding partner of the transmembrane TNF-$\alpha$ by comparison with the negative control indicates an increased risk of the presence of RA: IL-10, IL-4, IL-12.

Figure 1A:
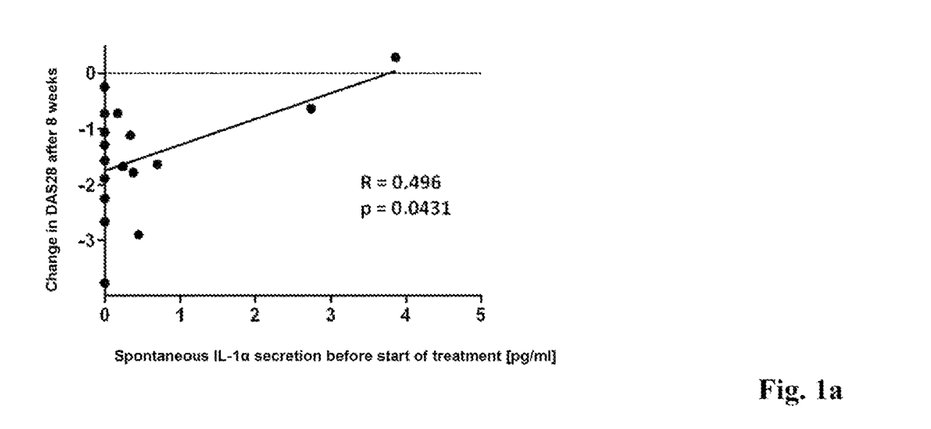
FIGS. 1a-c show that the spontaneous monocytic in vitro cytokine production and the spontaneous monocytic secretion of dissolved cytokine receptors before the start of treatment are inversely correlated with the response to a TNF inhibitor treatment, measured by the fall in the DAS28. The DAS28 (disease activity score) is a value for assessing the disease activity of rheumatoid arthritis, and is dependent on the number of tender joints (0-28 joints), the number of swollen joints (0-28), the erythrocyte sedimentation rate (mm/h) and the evaluations of the disease status by the patient. The higher the DAS28, the higher the disease activity.
Figure 1B:
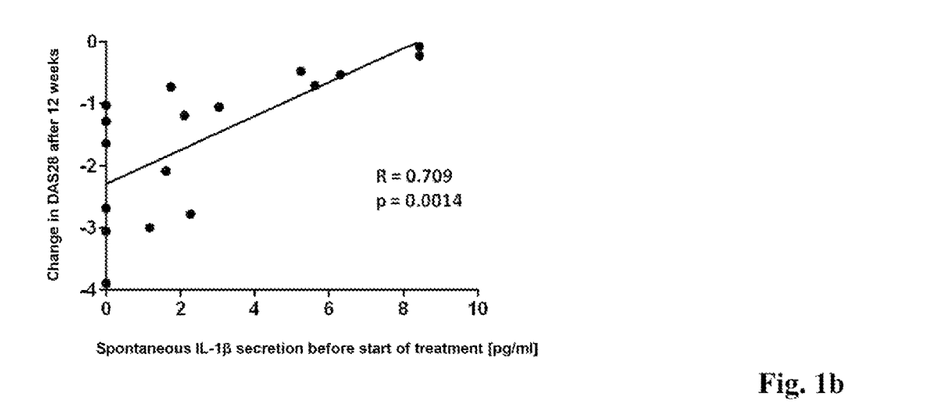
Figure 1C:
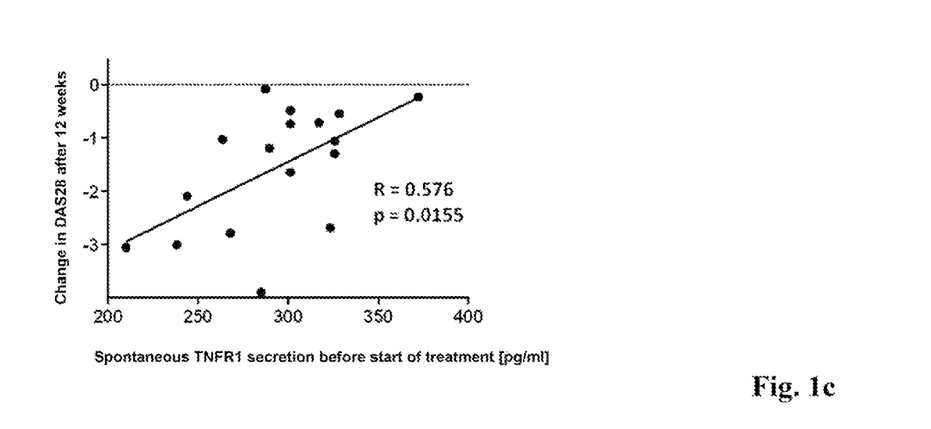
Figure 5:
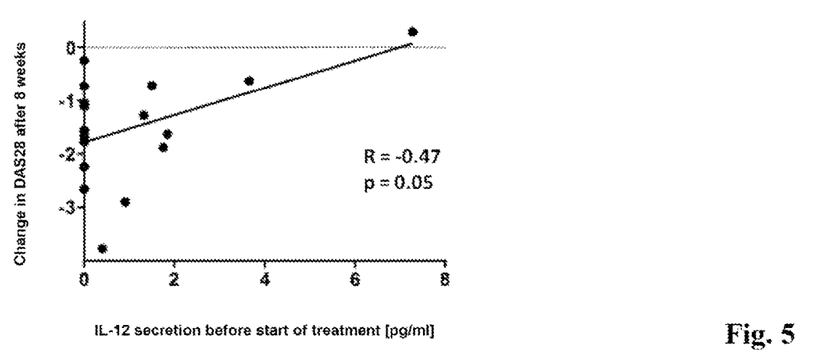
FIG. 5 shows that the level of the monocytic IL-12 secretion in vitro before treatment, induced by incubation with bonded TNFR2:Ig, is negatively correlated with the response to a TNF inhibitor treatment after 8 weeks.

The inventor's observations have shown that the spontaneous secretion of proinflammatory cytokines and of dissolved cytokine receptors (in particular of IL-1$\beta$, IL-1$\alpha$, TNFR1) of monocytes from patients having rheumatoid arthritis is inversely correlated with the response to a TNF inhibitor treatment, measured by the fall in the DAS28 (cf. FIGS. 1 and 5). For the following cytokines, a lower concentration in the residue of the sample from the test tube comprising the specific binding partner of the transmembrane TNF-$\alpha$ by comparison with the negative control indicates a poor response to a TNF inhibitor treatment: IL-1$\beta$, IL-1$\alpha$, TNFR1.

Figure 2:
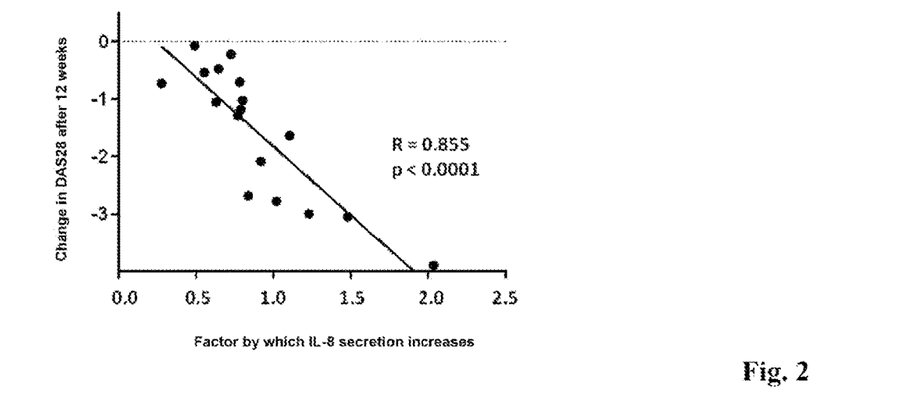
FIG. 2 shows that the increase in spontaneous monocytic IL-8 secretion in vitro, induced by soluble TNFR2:Ig, correlates with the decrease in the disease during treatment with the TNF inhibitor, measured by the fall in the DAS28. The higher the factor by which IL-8 secretion increases, the greater the fall in the DAS28 after 12 weeks of treatment, and so the better the response to the treatment.
Figure 3A:
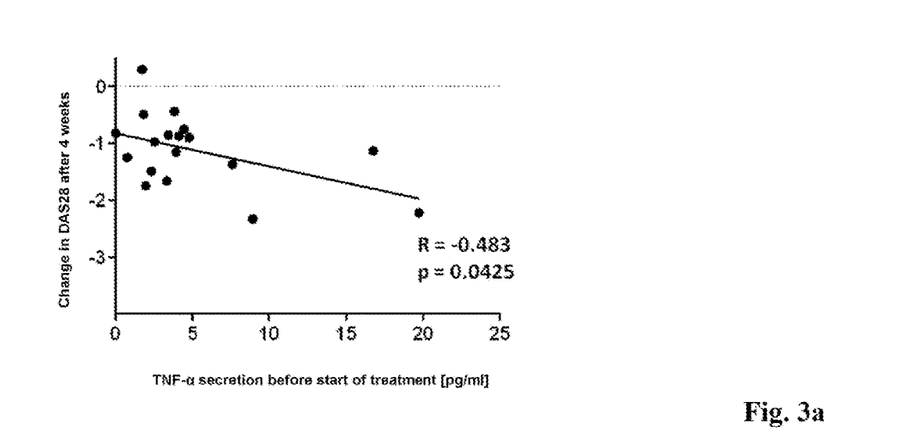
FIGS. 3a and 3b show that the level of the monocytic cytokine production in vitro before treatment, induced by incubation with soluble TNFR2:Ig, is positively correlated with the response to a TNF inhibitor treatment after 4 weeks, measured by the fall in the DAS28.
Figure 3B:
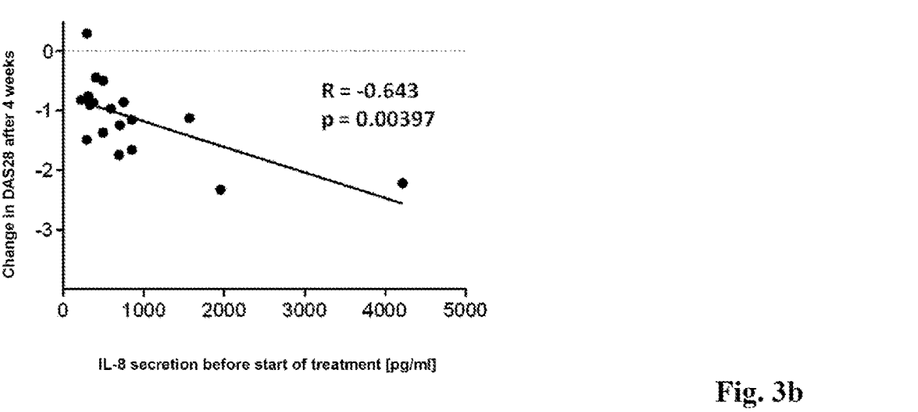
Figure 4:
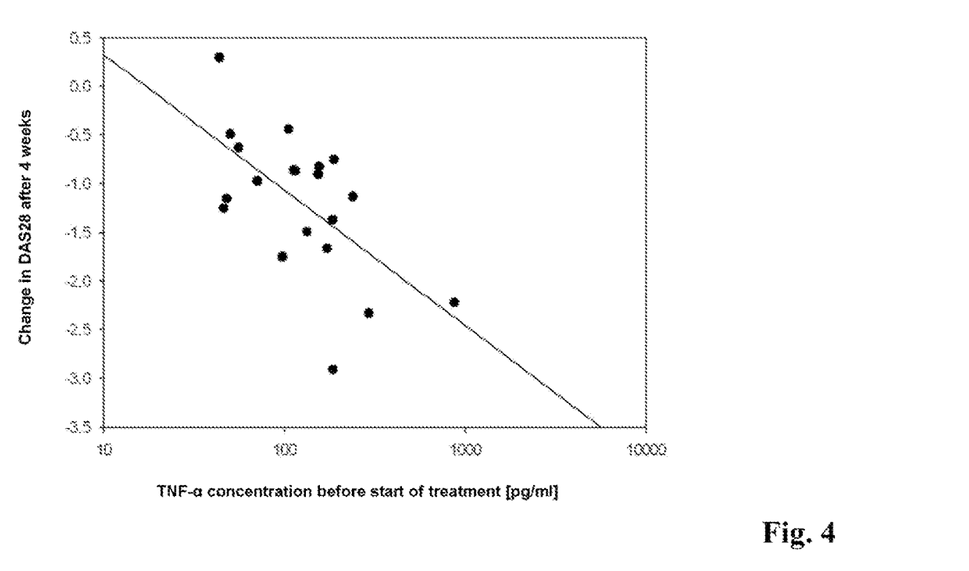
FIG. 4 shows that the TNF-α production triggered by tmTNF cross-linking and reverse signalling has a significant correlation with the response to therapeutic TNF inhibition, measured by the fall in the DAS28 after 4 weeks of treatment. The results show that a strong TNF-α response to tmTNF reverse signalling, induced by bonded TNFR2:Ig, is a predictor of a very good response to a treatment using TNF-α inhibitors.

The inventor's observations have further shown that the secretion of some proinflammatory cytokines and of dissolved cytokine receptors (in particular of IL-8, TNF-$\alpha$, TNFR1, IL-1R1) by monocytes of patients having rheumatoid arthritis after cross-linking of the transmembrane TNF-$\alpha$ with the specific binding partner of tm-TNF-$\alpha$ correlates with the response to a TNF inhibitor treatment, measured by the rise in the DAS28 (cf. FIGS. 2, 3 and 4). For the following cytokines, an increased concentration in the residue of the sample from the test tube comprising the specific binding partner of the transmembrane TNF-$\alpha$ by comparison with the negative control indicates a good response to a TNF inhibitor treatment: IL-8, TNF-$\alpha$, TNFR1, IL-1R1; particularly preferably of IL-8 (see FIG. 2).

Figure 6A:
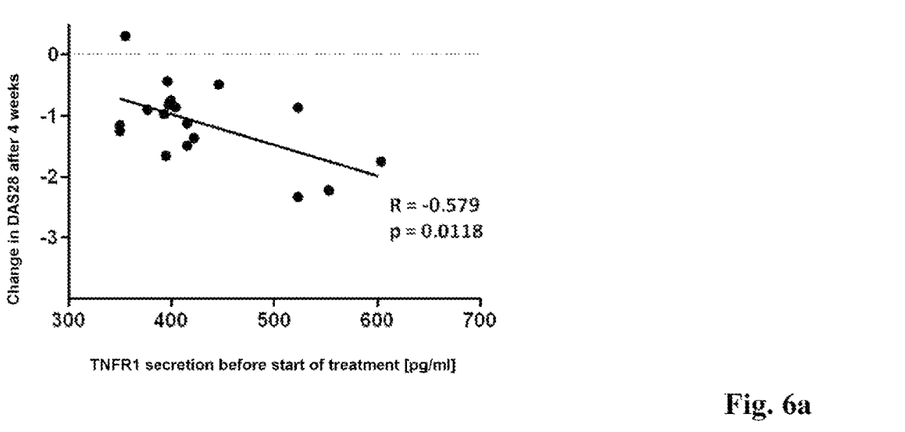
FIGS. 6a and 6b show that the level of monocytic secretion of soluble cytokine receptors in vitro before treatment, induced by incubation with bonded TNFR2:Ig, is positively correlated with the response to a TNF inhibitor treatment after 4 weeks.
Figure 6B:
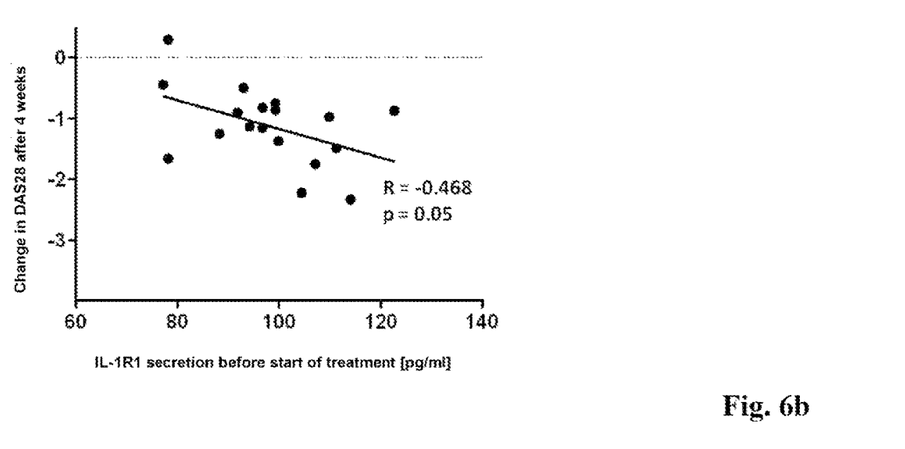

The inventor's observations have further shown that the secretion of some proinflammatory cytokines and of dissolved cytokine receptors (in particular of IL-12, IL-1β) by monocytes of patients having rheumatoid arthritis after cross-linking of the transmembrane TNF-α with the specific binding partner of tm-TNF-α correlates inversely with the response to a TNF inhibitor treatment, measured by the increase in the DAS28 (cf. FIGS. 5 and 6b). For the following cytokines, an increased concentration in the residue of the sample from the test tube comprising the specific binding partner of the transmembrane TNF-α by comparison with the negative control indicates a poor response to a TNF inhibitor treatment: IL-12, IL-1β.

To determine the concentration of TNF-α, a TNF-R2:Ig fusion protein is particularly preferably used as the specific binding partner of tmTNF-α.

Second analysis: triggering the CCR5 signal path

For said second analysis, a test tube contains a ligand of CCR5 (C-C motif chemokine receptor 5) as a stimulating agent. Said test tube preferably additionally contains a non-activating amount of a TLR ligand, in particular as described above. Preferably, the ligand of CCR5 is selected from RANTES (CCL5) or MIP-1α (CCL3). In this context, the ligand of CCR5 is preferably in the test tube in a soluble form. RANTES is used at a concentration of 0.1-10 µg/ml, preferably 0.8-1.2 µg/ml, more preferably 1 µg/ml, and MIP-1α is used at a concentration of between 0.1 nmol/l and 1 nmol/l. From the cell-free residue of the full blood samples from the test tubes, in said second analysis, the concentrations of at least one, preferably at least two, of the cytokines TNF-α, IL-6 and IFNγ, more preferably all of said cytokines, are determined. Optionally, the concentrations of at least one of the cytokines IL-1α, IL-1β, IL-23 and IL-8 are additionally determined.

Said second analysis is based on the observation that the stimulation of the chemokine receptor CCR5 on T cells and monocytes leads to the secretion of proinflammatory cytokines, in particular TNF-α, IL-6 and IFNγ, which is reduced in carriers of the genetic deletion (approximately 10% of Europeans). Therefore, in said second analysis, a reduced concentration of at least one, preferably at least two, more preferably all of the cytokines TNF-α, IL-6, IL-8 and IFNγ in the residue of the sample from the test tube comprising the ligand of CCR5 by comparison with the standard value, determined from the samples of 5 healthy individuals without the genetic deletion of CCR5, indicates a reduced risk that rheumatoid arthritis is present. The additional presence of a reduced concentration of at least one, preferably at least two, more preferably at least three of the cytokines IL-1α, IL-1β, IL-23 and IL-8 in the residue of the sample from the test tube comprising the ligand of CCR5 by comparison with the standard value of individuals without the genetic deletion of CCR5 indicates a partially reduced risk that RA is present. It is also possible to determine the concentration of one or more dissolved receptors, preferably selected from TNFR1, TNFR2, IL1R antagonist, IL-1R1, IL-1R2.

The prognostic evaluation of the disease progression on the basis of said second analysis is based on the observation that RA patients having a heterozygous deletion in the CCR5 gene have a mild disease progression and a good prognosis. Therefore, if the second analysis is carried out using a full blood sample, which verifiably originates from an RA patient (preferably from diagnosis by the first or third analysis), the presence of a reduced concentration of the detected cytokines (preferably all of the cytokines TNF-α, IL-6 and IFNγ) in the residue of the sample from the test tube comprising the ligand of CCR5 by comparison with the standard value of individuals without the genetic deletion of CCR5 indicates a good prognosis for the RA disease. Preferably, the concentration indicating a good prognosis of a cytokine in the test tube comprising the CCR5 ligand is at most ±10% of the concentration of the negative control.

Third analysis: triggering the GPRC6A signal path

For said third analysis, a test tube contains a divalent or trivalent cation, preferably in the form of a soluble salt of calcium, aluminium, gadolinium, strontium or magnesium, as a stimulating agent. The divalent or trivalent cations are preferably in the form of a soluble salt. More preferably, chloride, acetate or citrate are present as the anions. The use of one of the following salts is preferred, the respectively preferred working concentration being given in Table 1 below. The test tube contains an amount of the divalent or trivalent cation such that the respective working concentration is achieved after the volume of the full blood sample is added to the test tube.

TABLE 1

| Salt | Preferred working concentration |
| --- | --- |
| Calcium chloride | 1.5-2.5 mmol/l |
| Aluminium chloride (AlCl$_3$ × 6H$_2$O) | 300-1000 µmol/l |
| Gadolinium chloride hexahydrate | 300-1000 µmol/l |
| Magnesium chloride | 30-50 mmol/l |
| Strontium chloride | 0.2-0.5 mmol/l |

The divalent or trivalent cation is present in the test tube in a dissolved form.

Preferably, the test tube comprising the divalent or trivalent cation preferably additionally contains TLR ligands so as to improve the response of the cells to the specific stimulation. The test tube comprising the divalent or trivalent cation preferably additionally contains a non-activating amount of a TLR ligand, in particular as described above. Preferably, as an alternative, the test tube contains an activating amount of a TLR ligand, in particular selected from LPS, heat-killed *Listeria monocytogenes,* poly(I:C), flagellin and ssRNA40, as well as the stimulating agent. In this case, LPS is preferably contained at a concentration of 50-150 ng/ml, more preferably of 100 ng/ml. Heat-killed *Listeria monocytogenes* are preferably contained at a concentration of $10^7$ to $10^9$, more preferably of at most $10^8$ cells per ml. Poly(I:C) is preferably contained at a concentration of 8 to 12 µg/ml, more preferably of at most 1 µg/ml. Flagellin is preferably contained at a concentration of 0.8 to 1.2 µg/ml, more preferably of at most 1 µg/ml. ssRNA40 is preferably contained at a concentration of 0.8 to 1.2 µg/ml, more preferably of at most 1 µg/ml. In the context of the third analysis, reproducible results are achieved in particular by co-stimulation with a TLR ligand in an activating amount.

In said third analysis, the concentration of IL-1β is determined from the cell-free residue of the full blood samples from the test tube. Optionally, the concentrations of IL-6, IL-23 and/or TNF-α are additionally determined. It is also possible to determine the concentration of one or more dissolved receptors, preferably selected from TNFR1, TNFR2, IL1R antagonist, IL-1R1, IL-1R2.

Said third analysis is based on the observation that stimulation of the G-protein-coupled receptor GPRC6A in monocytes induces secretion of IL-1β, and also further of IL-6, IL-23 and/or TNF-α, in the presence of rheumatoid arthritis. Therefore, in the third analysis, a higher concentration of IL-1β in the residue of the sample of the test tube comprising the divalent or trivalent cation by comparison with the negative control indicates an increased risk of the presence of RA. The additional presence of a higher concentration of IL-6, IL-23 and/or TNF-α in the residue of the sample of the test tube comprising the divalent or trivalent cation by comparison with the negative control indicates an increased risk of the presence of RA. It is also possible to determine the concentration of one or more dissolved receptors, preferably selected from TNFR1, TNFR2, IL1R Antagonist, IL-1R1, IL-1R2. No soluble receptors can be detected in the negative control. Increased levels of the receptors indicate an increased risk in each case.

Figure 7:
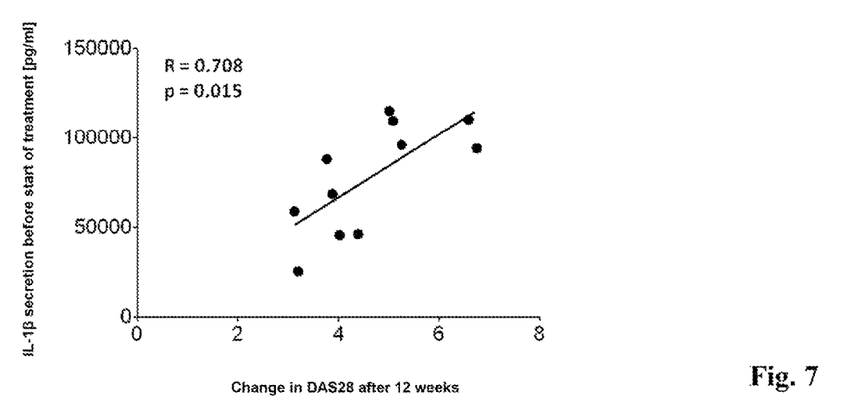
FIG. 7 shows that the stimulation of GPRC6A by way of increased extracellular calcium concentration is suitable as a prognostic parameter for the prognosis of the expected response to the treatment using a TNF inhibitor. The $Ca^{2+}$- induced IL-1β production is correlated with the fall in the DAS28 after 12 weeks of treatment, in other words with the response to the treatment.

The inventor's observations have demonstrated that stimulation of GPRC6A using increased extracellular cation concentrations is suitable as a prognostic parameter for the prognosis of the expected response to treatment using a TNF inhibitor (cf. FIG. 7). Therefore, in the third analysis, a higher concentration of IL-1β in the residue of the sample of the test tube comprising the divalent or trivalent cation in combination with an activating amount of a TLR ligand by comparison with the control comprising an activating amount of a TLR ligand (but without stimulating agent) indicates a good prognosis as regards the response to treatment using a TNF inhibitor.

Preferably, in the invention, at least one of the three aforementioned analyses is carried out. More preferably, at least the first analysis is carried out. Most preferably, the first and the second analysis are carried out in combination with one another. This advantageously makes possible a diagnostic and prognostic prediction in relation to the disease. To ensure better diagnosis and prognosis, all three analyses are carried out in the invention. If a plurality of analyses (first, second, third) are carried out, the stimulation using the respectively different stimulating agents takes place in separate test tubes.

The invention also includes a diagnostic kit by means of which at least sub-steps of at least one of the three aforementioned analyses (first, second, third analysis) can be carried out. The diagnostic kit according to the invention comprises:
  at least one test tube, containing:
    a stimulating agent, selected from a specific binding partner of tmTNF-α, preferably anti-TNF-α or TNFR2:Ig (preferably in a soluble or surface-bonded form, more preferably at least in a surface-bonded form), a CCR5 ligand, preferably RANTES or MIP-1α, and/or a divalent or trivalent cation, preferably of the metals calcium, aluminium, gadolinium, strontium or magnesium, preferably in the form of a soluble salt,
    at least one TLR ligand, preferably in a non-activating amount, as described above,
  at least two comparison test tubes, of which a first test tube is an untreated empty test tube for the negative control and a second test tube is for the positive control,
  optionally means for determining the cytokine concentration, preferably at least one ELISA plate for determining the concentration of at least one, preferably at least two, more preferably at least three of the cytokines TNFα, IL-8, IFNγ, IL-10, IL-1β and IL-6,
  optionally means for determining the concentration of dissolved receptors, selected from TNFR1, TNFR2, IL1R antagonist, IL-1R1, IL-1R2.

Preferably, the diagnostic kit according to the invention contains a plurality of test tubes having different ones of the stated stimulating agents.

A diagnostic kit according to the invention thus contains the necessary means for adding a stimulating agent to full blood samples of a human individual who is suspected to be suffering from rheumatoid arthritis. The samples can subsequently be incubated directly in the test tube at a temperature of 30-40° C. The cytokines formed during the incubation with the stimulating agent can be analysed using means which need not necessarily be part of the diagnostic kit. Preferably, the diagnostic kit also contains the means for the cytokine analysis.

Preferably, the diagnostic kit contains at least one test tube comprising anti-TNF-α as a stimulating agent. This preferably contains a non-activating amount of a TLR ligand as described above. Preferably, the test tube contains at most 1 ng/ml of the TLR ligand, in particular LPS. Preferably, the diagnostic kit contains at least one test tube comprising a ligand of CCL5 as the stimulating agent, preferably comprising RANTES or MIP-1α. This preferably contains a non-activating amount of a TLR ligand as described above. Preferably, the test tube contains at most 1 ng/ml of the TLR ligand, in particular LPS. Preferably, the diagnostic kit contains at least one test tube comprising a divalent or trivalent cation, preferably in the form of a soluble salt of calcium, aluminium, gadolinium, strontium or magnesium, as a stimulating agent. This preferably contains a TLR ligand, in particular LPS.

Preferably, the diagnostic kit contains at least one test tube comprising anti-TNF-α as a stimulating agent and at least one test tube comprising a ligand of CCL5, preferably comprising RANTES or MIP-1α.

More preferably, the diagnostic kit contains at least one test tube comprising anti-TNF-α as a stimulating agent, at least one test tube comprising a ligand of CCL5, preferably comprising RANTES or MIP-1α, and at least one test tube comprising a divalent or trivalent cation, preferably in the form of a soluble salt of calcium, aluminium, gadolinium, strontium or magnesium.

The test tubes in the diagnostic kit are designed as disclosed above. Preferably, the test tubes for use in a diagnostic kit according to the invention are designed as blood sampling tubes, preferably blood sampling tubes in accordance with the negative pressure system. The test tubes are preferably coated with a bioactive protein on the inside.

The test tube for the positive control preferably contains 200-900 ng lipopolysaccharide.

ELISA (enzyme-linked immunosorbent assay) methods are preferably used to determine the cytokine concentration in the cell-free residue obtained from the incubated full blood sample. For this purpose, for detecting a cytokine, the diagnostic kit according to the invention preferably contains equipment for detecting the respective cytokine, more preferably in the form of a respective ELISA plate. For this purpose, the ELISA plate (a 96-well plate) is preferably coated with an antibody which specifically binds the cytokine respectively to be detected. Therefore, the diagnostic kit preferably contains at least one ELISA plate which is coated with a specific antibody against a cytokine, selected from TNF-α, IL-8, IFNγ, IL-10, IL-1β or IL-6, or a dissolved receptor, selected from TNFR1, TNFR2, IL1R antagonist, IL-1R1, IL-1R2.

Preferably, a diagnostic kit according to the invention comprises:
  for the first analysis: at least one test tube comprising anti-TNF-α and equipment for detecting the concentration of one of the cytokines TNF-α, IL-8, IFNγ, IL-10 and IL-1β and/or one of the dissolved receptors TNFR1, TNFR2, IL1R antagonist, IL-1R1, IL-1R2 (preferably, the equipment for detecting the cytokine concentration or the concentration of the dissolved receptors is at least one ELISA plate; particularly preferably at least two, more preferably at least three, most preferably at least four ELISA plates are contained which are each provided for detecting the concentration of one of the aforementioned cytokines and/or dissolved receptors), for the second analysis: at least one test tube comprising a ligand of CCR5, preferably RANTES or MIP-1α, and equipment for detecting the concentration of one of the cytokines TNF-α, IL-6 and IFNγ and/or one of the dissolved receptors TNFR1, TNFR2, IL1R antagonist, IL-1R1, IL-1R2 (preferably, the equipment for detecting the cytokine concentration or the concentration of the dissolved receptors is at least one ELISA plate; particularly preferably at least two, more preferably at least three ELISA plates are contained which are each provided for detecting the concentration of one of the aforementioned cytokines and/or dissolved receptors), and/or for the third analysis: at least one test tube comprising a divalent or trivalent cation, preferably in the form of a soluble salt of calcium, aluminium, gadolinium, strontium or magnesium and equipment for detecting IL-1β, IL-6, IL-23, TNF-α, TNFR1, TNFR2, IL1R antagonist, IL-1R1 and/or IL-1R2, preferably in the form of an ELISA plate.

Optionally, the diagnostic kit according to the invention contains further equipment for the respective analysis, preferably ELISA plates, which are provided for detecting the aforementioned optionally analysed cytokines.

As well as the ELISA plate or plates, the diagnostic kit preferably further contains the following further means for determining the cytokine concentration by ELISA:
 a further antibody, which is not identical to the antibody on the ELISA plate, and which specifically binds the cytokine respectively to be detected. Said further antibody is preferably conjugated with a reporter enzyme (preferably horseradish peroxidase, alkaline phosphatase or glucose oxidase),
 a dye substrate (preferably p-nitrophenyl phosphate or o-phenylene diamine), and
 a standard containing the cytokine respectively to be detected (at a known concentration).

The invention also comprises the use of a diagnostic kit according to the invention for prognostic evaluation of the disease progression of rheumatoid arthritis, for diagnosis of rheumatoid arthritis and/or for prognostic evaluation of the severity of joint destruction in relation to rheumatoid arthritis. Particularly preferably, the invention is used for prognostic evaluation of the disease progression, in particular prognostic evaluation of the disease progression of rheumatoid arthritis during treatment using a TNF-blocking drug. This use preferably takes place within a method according to the invention.

The invention specifies a method and a diagnostic kit by means of which it is possible to make a prognostic prediction as to the disease progression of RA, and optionally additionally also an early diagnosis of RA, in a simple, cost-efficient in-tube test. It is further possible, in the context of the prognostic evaluation, to make a prediction as to the patient's response to a particular treatment (what is referred to as the "treatment response", in particular a prognosis of the response to a treatment using a TNF-inhibiting drug).

Detecting the cytokine production of cells in the peripheral blood makes possible a more robust prediction as to the disease status and the disease prognosis than the mere analysis of autoantibodies, for which corresponding immune cells are also always present in the peripheral blood depending on the inflammation status. Therefore, in the invention, the activation status of the immune cells involved in the disease is taken into account for the first time.

BRIEF DESCRIPTION OF THE DRAWINGS

The invention is to be explained in greater detail with reference to the following drawings and embodiments, but is not limited thereto.

FIG. 1a relates to the spontaneous IL-1α secretion, FIG. 1b relates to the spontaneous IL-1β secretion, and FIG. 1c relates to the spontaneous secretion of the dissolved cytokine receptor TNFR1.

An increased spontaneous monocytic in vitro cytokine production along with a spontaneous monocytic secretion of dissolved cytokine receptors is a diagnostic parameter associated with RA.

FIG. 3a relates to the TNFR2:Ig-induced TNF-α secretion and FIG. 3b relates to the TNFR2:Ig-induced IL-8 secretion before the start of treatment.

FIG. 6a relates to the TNFR2:Ig-induced TNFR1 secretion and FIG. 6b relates to the TNFR2:Ig-induced IL-1R1 secretion before the start of treatment.

EXAMPLE 1

Analysis of the TNF-α Concentration After Incubation with Bonded TNFR2:Ig 5 ml parent solution containing 100 µg/ml TNFR2:Ig as a stimulating agent are provided and incubated at 37° C. for 3 h. The residue is subsequently disposed of. It is expected that 125 µg TNFR2:Ig will bond to the surface. Subsequently, a soluble form of TNFR2:Ig is additionally added, for a final concentration in the culture medium of 40 µg/ml.

12 ml full blood are mixed with heparin and 0.1 ng/ml LPS immediately after being taken.

4 ml full blood in each case are subsequently added to the test tube containing bonded TNFR2:Ig, to an empty test tube as a negative control, and to a test tube containing lipopolysaccharide as a positive control.

This is followed by incubation at 37° C. for 16 h. Subsequently, the samples are centrifuged at 2000 rpm for 30 minutes and the concentration of TNF-α is determined from the cell-free residue by ELISA. An increased concentration in the residue of the sample from the test tube comprising TNFR2:Ig by comparison with the negative control indicates an increased risk of the presence of RA. A correlation with the response to therapeutic TNF inhibitors, measured by the fall in the DAS28 after 4 weeks of treatment, is shown in FIG. 4.

Table 2 shows TNF-α concentrations of five healthy people and five people having rheumatoid arthritis, in the test tube for the negative control and in the test tube comprising the stimulating agent in each case.

TABLE 1

|  |  | TNF-α concentration pg/ml |
|---|---|---|
| Healthy control 1 | Negative control | 1 |
|  | w/ TNFR2:Ig | 701 |
| Healthy control 2 | Negative control | 0 |
|  | w/ TNFR2:Ig | 363 |
| Healthy control 3 | Negative control | 14 |
|  | w/ TNFR2:Ig | 157 |
| Healthy control 4 | Negative control | 4 |
|  | w/ TNFR2:Ig | 248 |
| Healthy control 5 | Negative control | 29 |
|  | w/ TNFR2:Ig | 404 |
| RA patient 1 | Negative control | 31 |
|  | w/ TNFR2:Ig | 422 |
| RA patient 2 | Negative control | 49 |
|  | w/ TNFR2:Ig | 309 |
| RA patient 3 | Negative control | 19 |
|  | w/ TNFR2:Ig | 717 |
| RA patient 4 | Negative control | 19 |
|  | w/ TNFR2:Ig | 901 |
| RA patient 5 | Negative control | 3 |
|  | w/ TNFR2:Ig | 1298 |

EXAMPLE 2

Triggering the GPRC6A Signal Path 12 ml full blood are mixed with heparin and 0.1 ng/ml LPS immediately after being taken.

In a test tube, 100 ng/ml LPS are mixed with 2.5 mM calcium chloride.

4 ml full blood are subsequently added to the test tube containing 2.5 mM calcium chloride, resulting in a final concentration of 1.7 mM calcium chloride. A further 4 ml in each case are added to an empty test tube as a negative control and to a test tube containing lipopolysaccharide as a positive control.

This is followed by incubation at 37° C. for 16 h. Subsequently, the samples are centrifuged and the concentration of IL-1β is determined from the cell-free residue by ELISA. FIG. 7 shows that the $Ca^{2+}$-induced IL-1β production is correlated with the fall in the DAS28 after 12 weeks of treatment.

CITED NON-PATENT LITERATURE

Schellekens, G A, B A de Jong, F H van den Hoogen, L B van de Putte, and W J van Venrooij. "Citrulline Is An Essential Constituent of Antigenic Determinants Recognized by Rheumatoid Arthritis-specific Autoantibodies." *The Journal of clinical investigation* 101, no. 1 (1998): doi:10.1172/JCI1316.

Poulsom, Hannah, and Peter J Charles. "Antibodies to Citrullinated Vimentin Are a Specific and Sensitive Marker for the Diagnosis of Rheumatoid Arthritis." Clinical reviews in allergy & immunology 34, no. 1 (2008): doi:10.1007/s12016-007-8016-3.

Meusch, Undine, Manuela Rossol, Christoph Baerwald, Sunna Hauschildt, and Ulf Wagner. "Outside-to-inside Signaling Through Transmembrane Tumor Necrosis Factor Reverses Pathologic Interleukin-1 beta Production and Deficient Apoptosis of Rheumatoid Arthritis Monocytes." *Arthritis and rheumatism* 60, no. 9 (2009): doi:10.1002/art.24778.

The invention claimed is:

1. A method for prognostic evaluation of disease progression of rheumatoid arthritis (RA) and/or diagnosis of RA, the method comprising:
   (a) combining a non-activating concentration of a toll-like receptor ligand with a sample of whole blood of a human and transferring a volume of the whole blood with non-activating concentration of a toll-like receptor ligand into at least one test tube containing TNFR2: Ig as a stimulating agent, and as control samples, the same volume of whole blood from the human with non-activating concentration of a toll-like receptor ligand into an empty test tube as a negative control and a test tube containing an activation concentration of lipopolysaccharide (LPS) as a positive control respectively;
   (b) incubating the test tubes prepared in (a) at a temperature of 30-40°C.;
   (c) obtaining a cell-free reside from each whole blood sample and determining the concentration of TNF-α in the cell-free residue of each sample;
   wherein an increased concentration of TNF-α in the test sample when compared to the negative control indicates an increased risk of RA and that a good response to treatment with TNF inhibitor is likely.

2. Method of claim 1, wherein the toll-like receptor ligand is mixed with the whole blood sample at a maximum concentration of 0.1 ng/ml.

3. A diagnostic kit for prognostic evaluation of disease progression of rheumatoid arthritis, comprising:
   (i) at least one test tube containing TNFR2: Ig as stimulating agent;
   (ii) a test tube for a negative control and a test tube containing an activation concentration of lipopolysaccharide (LPS) for the positive control; and
   (iii) a toll-like receptor ligand for addition at a non-activation concentration to a whole blood sample.

4. A diagnostic kit according to claims 3, wherein the TNFR2: Ig is in a surface-bonded form.

5. A Method for evaluation of disease progression of reheumatoid arthritis (RA) and /or diagnosis of RA, the method comprising:
  (a) combining a whole blood sample from a human with a non-activating concentration of a toll-like receptor ligand and transferring a volume of said whole blood sample containing a non-activation concentration of a toll-like receptor ligand into at least one test tube containing TNFR2-Ig, and as negative and positive control samples, and equal volume of said whole blood sample with a non-activation concentration of a toll-like receptor ligand into an empty test tube and a test tube containing an activation concentration of lipopolysaccaharide, respectively;
  (b) incubating the test sample and negative and positive controls at a temperature of 30-40° C. for a time sufficient for cells in the whole blood to be stimulated by the TNFR2-Ig;
  (c) obtaining a cell-free residue from each test sample and negative and positive controls and determining the concentration of TNF-α in said samples; and
  (d) identifying an increased risk of RA and/or the likelihood of a good response to treatment of the human with TNF inhibitor when there is higher concentration of TNF-α in the test sample when compared to the negative control.

6. The method of claim 5, wherein the time sufficient for cells in the whole blood to be stimulated by the stimulating agent is between 4 and 48 hours.

7. The method of claim 6, wherein the time sufficient for cells in the whole blood to be stimulated by the stimulating agent is between 12 and 24 hours.

8. A diagnostic kit according to claim 3 additionally comprising an ELISA plate for determining the concentration of TNF-α.

* * * * *